United States Patent [19]

Pastrone

[11] Patent Number: 4,703,775
[45] Date of Patent: Nov. 3, 1987

[54] LIQUID FLOW REGULATOR

[75] Inventor: Giovanni Pastrone, Los Gatos, Calif.

[73] Assignee: Abbott Laboratories, North Chicago, Ill.

[21] Appl. No.: 856,723

[22] Filed: Apr. 25, 1986

Related U.S. Application Data

[63] Continuation-in-part of Ser. No. 776,399, Sep. 16, 1985, abandoned, which is a continuation-in-part of Ser. No. 626,266, Jun. 29, 1984, Pat. No. 4,552,336.

[51] Int. Cl.$^4$ .................... F16K 7/02; F16K 31/50
[52] U.S. Cl. ................... 137/625.3; 251/121;
251/215; 251/205; 251/331; 411/510; 411/512;
74/424.8 A; 74/424.8 VA; 604/32; 604/33
[58] Field of Search .............. 74/424.8 A, 424.8 VA;
411/508, 509, 510, 512; 251/96, 229, 215, 331,
205, 904, 121; 604/32, 33, 248, 249, 236, 256;
138/46; 137/625.3

[56] References Cited

U.S. PATENT DOCUMENTS

| | | |
|---|---|---|
| 686,391 | 11/1901 | Cox .................................. 74/424.8 A |
| 2,276,195 | 3/1942 | Holmes ........................... 74/424.8 A |
| 2,771,878 | 7/1956 | Folland . |
| 3,058,431 | 7/1958 | Eddy . |
| 3,460,526 | 7/1965 | McKirdy et al. . |
| 3,620,500 | 2/1970 | Santomieri . |
| 3,841,354 | 9/1974 | McDonnell . |
| 3,851,668 | 12/1974 | Benjamin . |
| 3,880,401 | 4/1975 | Wiltse . |
| 3,985,336 | 10/1976 | Bentley . |
| 4,223,813 | 9/1980 | Garrett et al. . |
| 4,300,552 | 11/1981 | Cannon . |
| 4,600,344 | 7/1986 | Sutenbach et al. ............. 411/510 X |

Primary Examiner—Arnold Rosenthal
Attorney, Agent, or Firm—Martin L. Katz; Robert W. Stevenson

[57] ABSTRACT

A liquid flow regulator has a housing including an axial bore, an inlet, an outlet and a plurality of axial grooves opening endwise of the inlet and laterally of the housing into the bore. The grooves, which have different axial lengths, taper axially so that the cross-sectional area of each groove gradually decreases from the inlet to nothing at a point where the groove merges with the bore. An elastomeric stock fits within the bore. A plunger for expanding the sock radially outward into sealing engagement with the housing adjacent the bore is axially movable within the bore. Flow through the grooves and the bore is regulated by the axial position of the plunger and the minimum cross-sectional area of the tapered, axial grooves at the axial location where the sock seals the bore. Axial adjustment of the plunger sequentially opens and closes passage from the grooves through the bore to the bore outlet. The upper end of the plunger is provided with threads for engagement with internal threading in a passageway so that rotation of the plunger adjusts its axial position for control of the flow. The connection between the plunger and passageway threads is flexible so that the threads can be flexed out of engagement with each other when it is desired to axially and non-rotatively move the plunger to quickly place the regulator in a fully open or fully closed condition.

18 Claims, 15 Drawing Figures

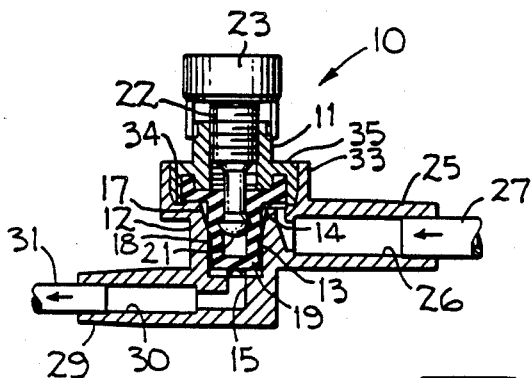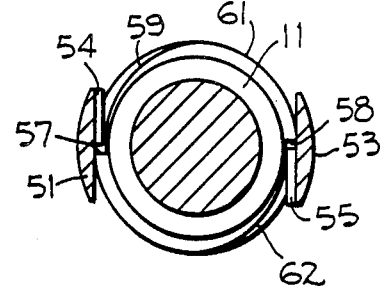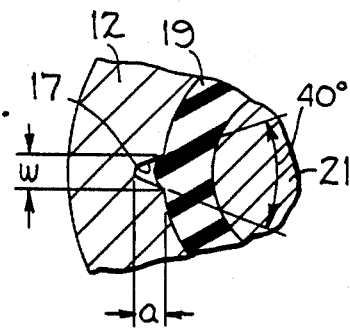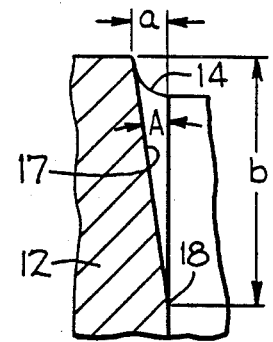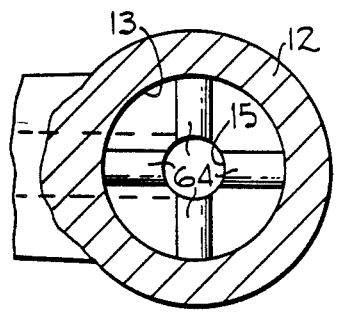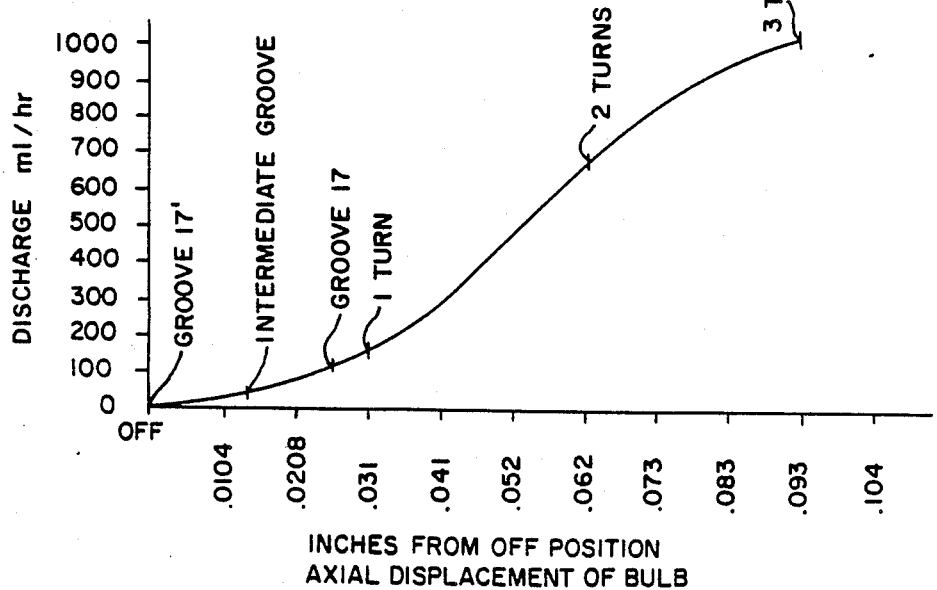

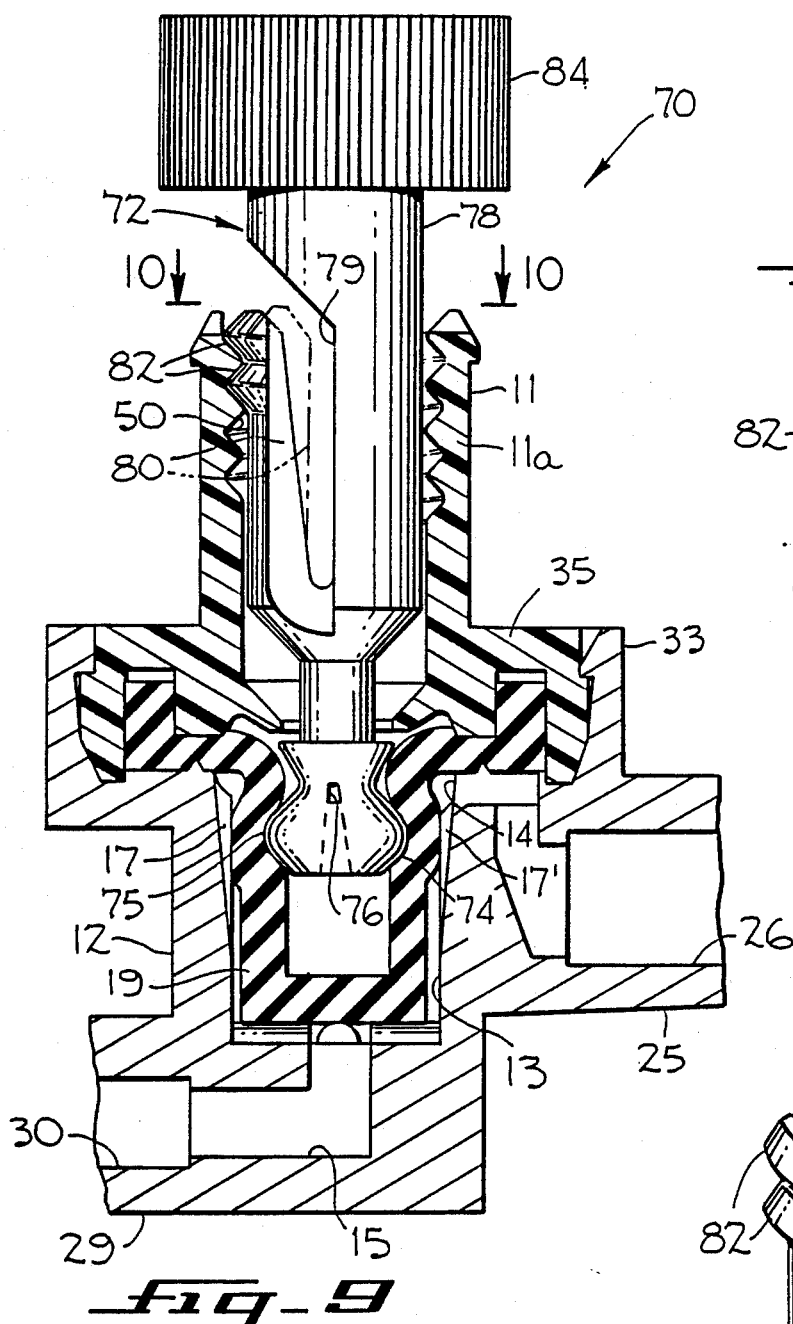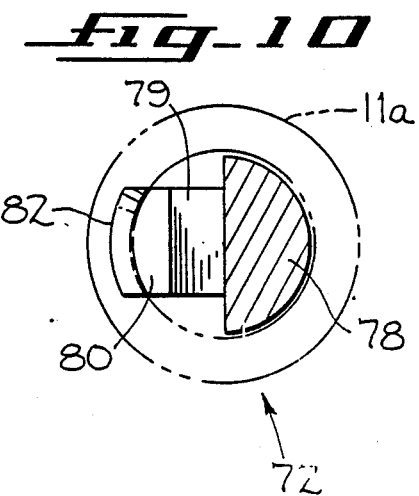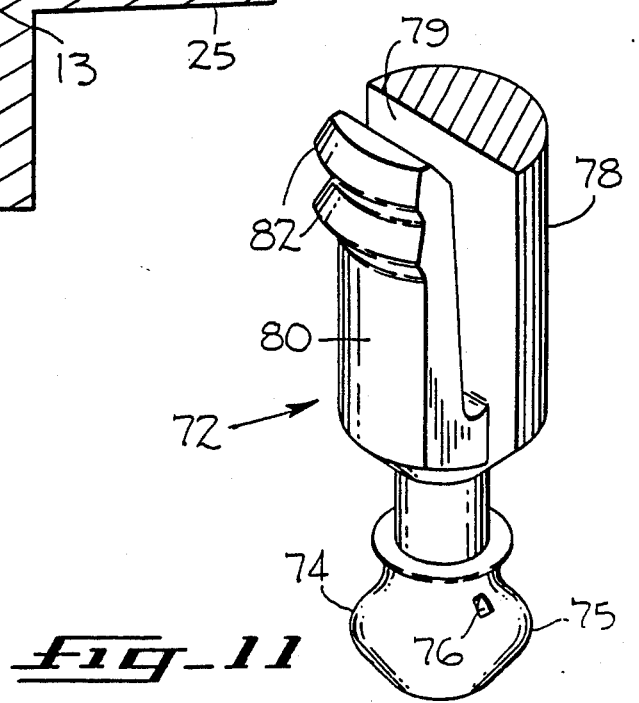

LIQUID FLOW REGULATOR

CROSS-REFERENCE TO RELATED APPLICATION

This application is a continuation-in-part of U.S. patent application Ser. No. 776,399, filed Sept. 16, 1985, and now abandoned, entitled "Liquid Flow Regulator" which was a continuation in part of U.S. patent application Ser. No. 626,266, filed June 29, 1984, entitled "Liquid Flow Regulator" now U.S. Pat. No. 4,552,336.

BACKGROUND OF THE INVENTION

1. Field of the Invention

This invention relates generally to flow control valves. More specifically, it concerns a liquid flow regulator that blocks or controls the flow therethrough at precise discharge rates, suitable for intravenous infusion systems.

2. Description of the Prior Art

Medical treatment may require intravenous infusion of liquids into a patient's blood system for replacing blood, providing food energy, correcting acidity, or introducing drugs. The rate of introduction of the liquid must be carefully controlled for the health or safety of the patient. Pinch clamps acting directly upon a conduit made of plastic tubing have been used to control liquid flow within the conduit. Such clamps have been unreliable and require frequent attention to maintain proper adjustment. Various flow control devices have been developed to provide a more uniform flow rate.

U.S. Pat. No. 3,880,401, issued Apr. 29, 1975 to Harold L. Wiltse, shows a combined flow metering and shut-off valve. Inner and outer valve parts are axially movable relative to one another to effect relative axial movement of a metering valve plug on one part into and from a metering bore in the other part for regulating and blocking flow through the valve passage. A tapered groove portion on the valve plug forms with the wall of the metering bore a flow passage whose effective cross-sectional flow area increases as the plug retracts and decreases as the plug enters the bore.

U.S. Pat. No. 4,223,813, issued Sept. 23, 1980 to Scott T. Garrett et al., discloses a fluid-flow limiting device having a rigid plastic part and a stretchable elastomeric membrane that together define a metering chamber with an inlet and an outlet. A plastic section fuses to the rigid plastic part and the membrane is enveloped between the part and section. Movable valve members fit through openings in the section to the membrane to stretch it and close off the inlet or the outlet, as appropriate.

U.S. Pat. No. 4,300,552, issued Nov. 17, 1981 to Raymond E. Cannon, shows an intravenous flow control apparatus having a button with V-shaped notches. A flexible diaphragm is positioned above the notches and can be forced against the button and partially into the notches by a pusher rod so as to control the rate at which fluid flows through the notches from an input line to an output line.

U.S. Pat. No. 3,058,431 to Eddy discloses a valve which utilizes a tubular valve head of rubber or rubber-like material and which can be expanded outwardly by a longitudinally movable sphere extending within the valve head to block flow through the narrow cylindrical passageway surrounding the valve head.

U.S. Pat. No. 3,985,336 to Bentley discloses a drip irrigation valve including a tubular outer member having a longitudinally extending groove along its inner wall of continuously variable cross-sectional area. An inner member is axially movable within the outer member and includes a resilient O-ring which engages the wall of the outer member at the groove to close off flow through the valve except through the groove passageway at the O-ring. By axially shifting the position of the inner member relative to the groove the flow rate is controlled.

U.S. Pat. No. 3,851,668 to Benjamin discloses a flow control device which operates by moving a rigid ball axially within a flexible tube having channels of varying lengths provide in the interior wall of the tube for passing the liquid flow past the ball.

Other patents showing flow control devices for intravenous systems include U.S. Pat. No. 2,771,878, issued Nov. 27, 1956 to W. E. Folland et al.; U.S. Pat. No. 3,460,526, issued Aug. 12, 1969 to R. W. McKirdy et al,; U.S. Pat. No. 3,620,500, issued Nov. 16, 1971; and U.S. Pat. No. 3,841,354, issued Oct. 15, 1974 to Roy Edward McDonnell.

SUMMARY OF THE INVENTION

In accordance with the present invention, there is provided a liquid flow regulator having a housing with an axial bore. An inlet is located adjacent one end of the bore, and an outlet is located at the opposite end of the bore. The housing has at least one axial groove opening endwise into the inlet and laterally of the housing into the bore. The groove is tapered from the inlet to the bore so that the groove cross-sectional area gradually decreases to nothing where it merges with the bore. An elastomeric member fits tightly about a plunger within the bore with the upper end of the plunger being provided with threads engaged within a threaded passage in the housing. The plunger is movable axially of the bore by rotation thereof for expanding the elastomeric member radially outward into sealing engagement with the housing adjacent the bore at different axial locations along the bore. Flow through the groove and the bore is regulated by the axial position of the plunger and the minimum cross-sectional area of the tapered, axial groove at the axial location where the elastomeric member seals the bore. The connection between the upper end of the plunger and the threaded passage is laterally flexible so that the plunger can be directly moved axially without rotation to rapidly move the flow regulator from a fully open position to a fully closed position or vice versa.

In a preferred embodiment of the invention, the housing has a plurality of axial grooves opening endwise into the inlet and laterally of the housing into the bore. The grooves are tapered from the inlet end to the bore so that the cross-sectional area of each groove gradually decreases to nothing where the groove merges with the bore. The grooves have different axial lengths. Axial adjustment of the elastomeric member sequentially opens and closes passage from the grooves through the bore outlet.

BRIEF DESCRIPTION OF THE DRAWINGS

FIG. 3 is a reduced axial section of the liquid flow regulator shown in FIGS. 1 and 2;

FIG. 4 is a reduced horizontal section taken on the line 4—4 of FIG. 1;

FIG. 5 is an enlarged horizontal section taken on the line 5—5 of FIG. 1;

FIG. 6 is an enlarged axial section through one of the tapered grooves of the regulator shown in FIGS. 1, 2, and 3;

FIG. 7 is a horizontal section taken on the line 7—7 of FIG. 1;

FIG. 8 is a diagram of the regulator flow characteristics showing the discharge in relationship to the axial displacement of the bulb from a flow shut-off position;

FIG. 9 is an axial section, with a portion broken away, of a liquid flow regulator embodying the present invention;

FIG. 10 is a section taken on line 10—10 of FIG. 9;

FIG. 11 is an isometric view of the plunger of the liquid flow regulator of FIG. 9;

DESCRIPTION OF THE PREFERRED EMBODIMENT

Figure 2:
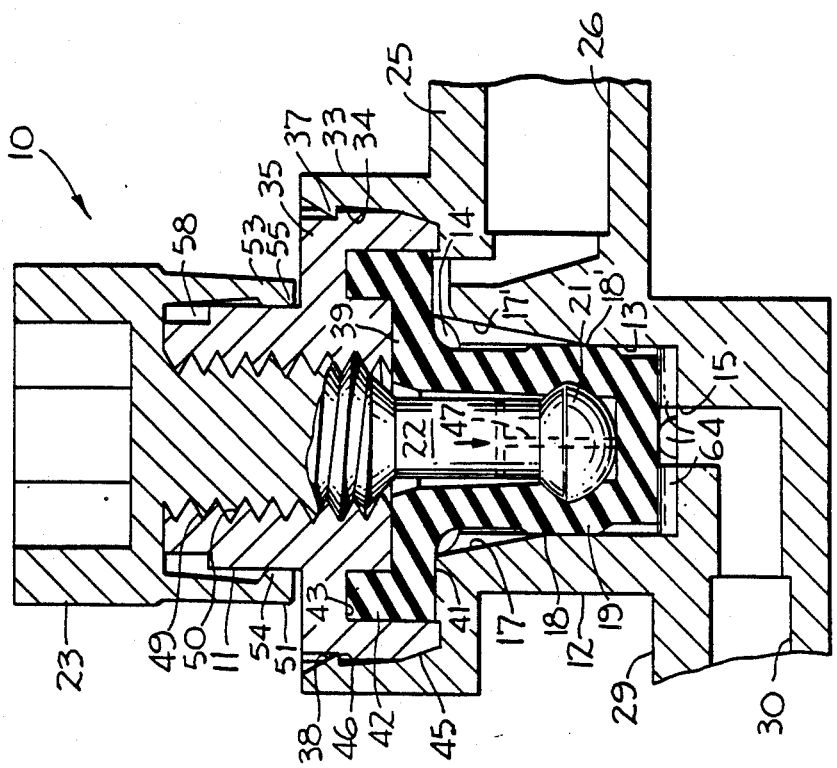
FIG. 2 is an axial section of the liquid flow regulator similar to FIG. 1 but showing the regulator in its flow shut-off position.
Figure 1:
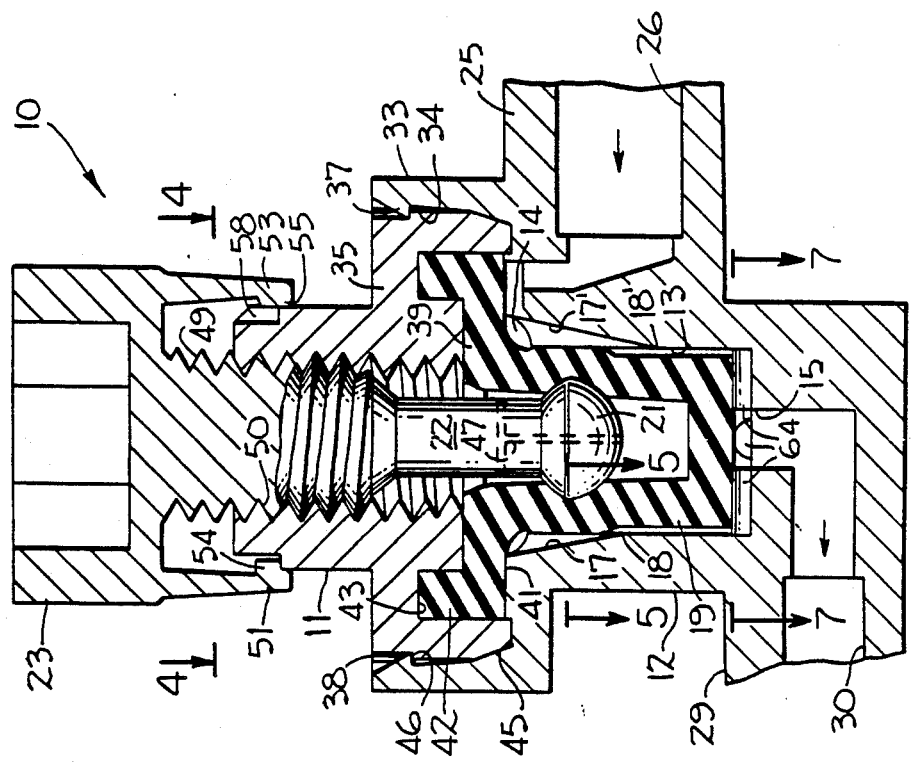
FIG. 1 is an axial section, with a portion broken away, of a liquid flow regulator of the type of the present invention in its open flow position.
Figure 12:
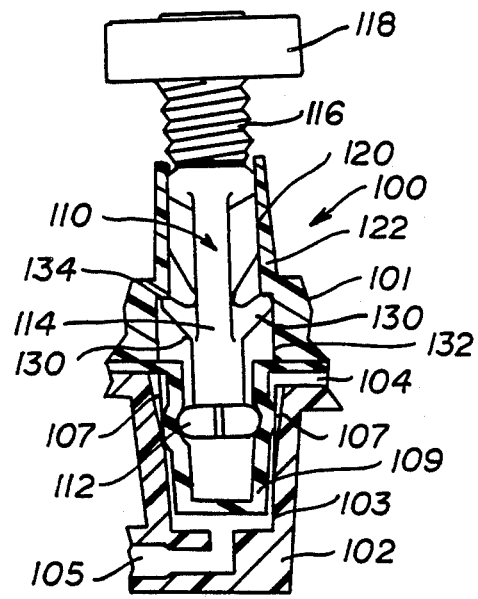
FIG. 12 is an axial section of an alternative embodiment of a liquid flow regulator of the present invention.

A liquid flow regulator of the general type of the present invention, indicated generally by reference numeral 10, is shown in FIGS. 1, 2, and 3. The regulator has a housing formed by an upper part 11 and a lower part 12. Within the lower part is an axial bore 13. An inlet 14 is provided adjacent the upper end of the bore and a central outlet 15 is provided at the lower end of the bore. At least one axial groove 17 opens endwise into the inlet and laterally of the housing lower part into the bore. The groove tapers in lateral penetration into the housing so that the groove cross-sectional area gradually decreases to nothing at a point 18 where the groove merges into the bore. An elastomeric sock 19 is fitted within the bore. Mounted for movement axially of the bore and positioned within the sock is a plunger that includes a bulb 21 mounted on a stem 22 that threadedly fits through the housing upper part to where a knob 23 is attached for rotating the stem. As the bulb moves axially of the bore, it forces the sock radially outward into sealing engagement with the lower housing part adjacent the bore. Thus, flow through the groove and the bore is regulated by the axial position of the bulb and the minimum or effective cross-sectional area of the tapered axial groove at the location where the sock seals the bore.

With reference to FIG. 3, the housing lower part 12 has a barrel 25 that forms a socket 26 for receiving supply tubing 27. This tubing is connected to a source, not shown, such as a liquid reservoir located at an elevation that provides a suitable gravitational head above the regulator. A barrel 29 on the housing lower part provides a socket 30 for receiving discharge tubing 31 that can be intravenous tubing leading to a needle, not shown, for insertion into a patient. A barrel 33 is provided at the top of the housing lower part. This barrel is coaxial with the axial bore 13 and forms a socket 34 for receiving a base portion 35 of the housing upper part 11.

Looking again at FIGS. 1 and 2, a lip 37 projects radially from the barrel 33 at the mouth of the socket 34. The lip has a beveled upper surface 38 to facilitate insertion of the base portion 35. The elastomeric sock 19 has a radial portion 39 that extends over the inlet 14 and seats on a base 41 of the socket. Extending axially from the radial portion of the elastomeric sock is an anchor flange 42 that interlocks within a corresponding recess 43 in the bottom of the base portion. A chamber 45 is provided at the bottom peripheral edge of the base portion to facilitate insertion into the socket, and a radial step 46 is provided on the base portion periphery to interlock with the lip. Upon insertion of the base portion into the socket, the lip is spread outwardly until it can pass over the radial step. At the time the lip and the step snap together, the upper part 11 and the lower part 12 of the housing are interlocked, and the elastomeric sock is locked in place within the bore 13.

A vent 47 extends from the bottom of the bulb 21 to a location laterally of the stem 22 to provide pressure relief when the bulb moves axially downward into the elastomeric sock 19. The stem has external threads 49 and the housing upper part 11 has internal threads 50 that mate for moving the stem axially of the bore upon rotation of the knob 23.

In the FIG. 1 flow regulator, it is desirable to limit withdrawal of the bulb 21 from the axial bore 13 by disabling the rotation of the stem 22. Depending from the knob 23 are pair of legs 51 and 53. A lug 54 projects laterally from leg 51 towards leg 53. A lug 55 projects laterally from leg 53 towards leg 51. These lugs are offset on opposite sides of a diametrical line between the legs, as shown in FIG. 4. A pair of stops 57 and 58 are located near the top of the housing upper part 11 for engaging the lugs when the stem is rotated counterclockwise. A cam surface 59 extends from the stop 57 to the outer periphery 61 of the housing upper part, and cam surface 62 extends from the stop 58 to the outer periphery. These cam surfaces force the lugs radially outward upon clockwise rotation of the stem 22. The lugs can travel downward following the outer periphery below the stops. When the lugs are elevated and engage the stops, further counterclockwise rotation is prevented, but the legs can be spread apart to enable further counterclockwise rotation for disassembly of the stem from the housing upper part.

Looking again at FIG. 1, the inlet 14 has an annular shape that encircles the top of the bore 13 and a portion of the elastomeric sock 19. Liquid flows to the inlet from the supply tubing socket 26. The axial groove 17 has a V-shaped cross-section with a central angle of about 40° in the particular embodiment illustrated, as seen in FIG. 5. This groove tapers in both horizontal width (w) and lateral penetration (a) into the housing over the length (b), the base line of the groove making an angle (A) with a vertical line, as shown in FIG. 6, so that the effective cross-sectional area of the groove gradually decreases from the inlet to nothing at point 18 where the groove merges into the bore. While one axial groove is essential, any number of grooves can be used to obtain the desired flow characteristics, and the grooves may be of different shapes or sizes or (as in the case illustrated in FIGS. 1 and 2) they may terminate at different levels. Thus, a second axial groove 17', shown in FIG. 1, tapers to a point 18' where the groove merges into the bore, the point 18' being lower than the point 18 thus making the groove 17' larger than the groove 17 to permit greater flow therethrough. Similarly, a third axial groove, not shown, can be provided which might terminate at some different elevation, e.g., intermediate of 18 and 18'. In the particular embodiment shown, each groove has a lateral penetration (a) (FIG. 5) of 0.015 inches. The grooves have different angles (A) (FIG. 6) with the vertical. Groove 17 has a length (b) of 0.145 inches and forms an angle (A) of 10 degrees. The intermediate groove (not shown) has a length (b) of 0.157 inches and forms an angle (A) of 9 degrees. Groove 17' has a length (b) of 0.170 inches and forms an angle (A) of 8 degrees. Thus, as the bulb 21 is elevated from the shut-off position, as shown in FIG. 2, to the open position, shown in FIG. 1, groove 17', the intermediate groove not shown, and groove 17 would open in sequence. Conversely, when the bulb is lowered from the open position to the shut-off position, groove 17, the intermediate groove not shown, and groove 17' would be closed in sequence.

The elastomeric sock 19 is supported above the bottom of the bore 13 by radial ribs 64, shown in FIG. 1, that project upwardly from the housing part 12 into the bore. As shown in FIG. 7, these ribs extend from the outer periphery of the bore to the central bore outlet 15. Thus liquid can flow between the ribs and under the sock from the bore periphery to the bore outlet.

FIG. 8 shows the flow characteristics of the regulator 10 (with the three flow grooves 17 as previously specified), under an 18 inch gravitational head of liquid pressure, as the bulb 21 is elevated from the off-position shown in FIG. 2. Upon counterclockwise rotation of the knob 23, groove 17' is opened. The flow through the groove increases at the location where the elastomeric sock 19 seals the bore 13. The intermediate groove, not shown, and groove 17 open in sequence upon further elevation of the bulb. The three grooves are opened within one turn (360°) of the knob so that thereafter the discharge rapidly builds up. Upon three turns of the knob, a discharge of 1039 ml/hr is obtained. The slope of the curve indicates that the discharge builds up slowly at first at the low flow rates (where sensitivity of the adjustment mechanism is most important) and more rapidly thereafter. With each rotational movement of the knob, the discharge is adjusted. A conventional drip chamber, not shown, can be provided to determine the number of drops per minute (and thereby the actual flow rate), and the desired flow rate can thus be obtained by adjusting the regulator until the desired rate is observed.

A flow regulator 70, embodying the present invention, is shown in FIGS. 9, 10, and 11. The general construction of the flow regulator 70 is similar to the flow regulator 10 shown in FIGS. 1-7, and the same reference numerals will be used to describe the similar parts thereof.

Thus, it will be seen that the regulator 70 is formed with a housing having an upper part 11 and a lower part 12 with the lower part including an axial bore 13. As with the regulator 10, an inlet 14 is provided at the upper end of the bore and an outlet 15 is provided at the lower end of the bore. Axial grooves 17 of differing lengths (grooves 17 and 17' being shown in FIG. 9) are provided about the bore 13, such grooves being identical to the grooves previously described with respect to regulator 10. An elastomeric sock 19 is fitted within the bore and is clamped between the upper and lower housing parts 11 and 12 as shown in FIG. 9. Fluid is directed into the regulator from conventional tubing connected in a socket 26 in inlet barrel 25, and fluid is discharged therefrom through conventional tubing connected within a socket 30 in discharge barrel 29. A barrel 33 is provided at the top of the housing lower part coaxial with the axial bore 13 to form the socket for reception of the base portion 35 of the housing upper part 11. Also, as with the previously described regulator 10, housing upper part 11 includes an upright hub 11a having internal threading 50 for reception of the plunger and control of the axial movement thereof.

The plunger 72 of the flow regulator shown in FIGS. 9-11 differs from the plunger of the previously described regulator 10 and will thus be described in detail. It will be seen that the lower end of the plunger includes a head 74 having an enlarged central projecting rib 75 for forcing the elastomeric sock 19 into flow restricting engagement with the bore. An air flow passage 76 from the flat bottom of the plunger to a port above the compressive rib 75 is provided through the head 74 so as to prevent air from being compressed within the elastomeric sock 19 as the plunger is lowered as with the previously described flow regulator 10. The upper portion of the plunger is provided with a stem 78 which is split longitudinally by a groove 79 so as to leave a relatively thin, flexible flange 80 well spaced from the main body of the stem. The upper end of the flange 80 is provided with a pair of outwardly projecting teeth or threads 82 which are adapted to be rotatively engaged in the threading 50 of upper housing barrel 11a (FIG. 9). The upper end of the stem 78 is provided with an enlarged, knurled knob 84 which can be gripped and rotated to thereby lower or elevate the plunger as the teeth 82 rotate in the threads 50. As with the previously described flow regulator, this rotational movement shifts the axial position of the plunger head within the elastomeric sock 19 thereby either slightly increasing or decreasing the flow through the device.

It is a significant feature of the present invention that the plunger 72 may be adapted to be directly moved from its uppermost position, where the flow regulator is open to unrestricted flow through each of the grooves 17, to its lowermost position wherein the plunger head 74 completely closes off all of the grooves 17 and totally restricts flow through the regulator. This can be accomplished without any rotation of the plunger by applying a direct axial force to the knob 84 to either push the plunger directly down to close off the flow or to pull it up into the uppermost position to permit free flow. As will be seen by the phantom line position of flange 80 in FIG. 9, the flange 80 flexes inwardly under such axial upward or downward force under the inwardly directed camming forces against the teeth 82, thereby permitting the teeth 82 to slide over the internal thread 50 in the housing.

It will thereby be seen that the flow regulator 70 of FIGS. 9-11 not only acts as a highly accurate and precise flow control device when the plunger 72 is rotated to change the groove 17 flow control openings but can also be utilized as a direct shut-off or free flow device by a simple linear movement of the plunger. This has a particular advantage in infusion devices that require a high degree of flexibility where the flow regulator 70 can be used alternatively with a secondary flow controlling mechanism such as a positive displacement pump. Under this arrangement the flow control device can be used as the sole means of control when the pump is not used (i.e., inlet and outlet pots locked open), or the flow control device can be locked open (i.e., plunger 72 in uppermost position) to provide sole control in the pump, or the flow control device can act as the basic shut-off mechanism for the device (i.e., plunger 72 in its lowermost position).

Another alternative for the flow control regulator of the present invention is illustrated in FIGS. 12-15. The modified regulator 100 includes an upper housing portion 101 and a lower housing portion 102. Both housing portions are made of an injection moldable resinous thermoplastic or thermostatic material. Lower housing portion 102 is identical to lower housing portion 12 of FIG. 9. It includes an axial bore 103. An inlet 104 is located adjacent the upper end of bore 103 and outlet 105 is positioned at the lower end of bore 103. At least one groove 107 extends from the inlet downwardly along the sides of bore 103. Groove 107 tapers in the cross sectional area so that the groove cross sectional area gradually tapers to nothing at point 108 where the groove merges into the bore. Sock 109 is fitted within the bore.

Plunger 110 is mounted in sock 109, and is made of an injection-moldable plastic material. Plunger 110 includes a head 112 mounted on a stem 114. Stem 114 includes a threaded portion 116 and a knob 118. Stem 114 is mounted within an elongated bore 120 through a split tubular member 122 which is part of upper housing portion 101.

Figure 13:
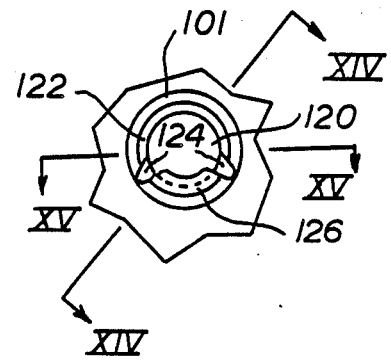
FIG. 13 is a top plan detailed view of the upper part of the liquid flow regulator of FIG. 12 taken along the plane of line 13—13 of FIG. 12, with the plunger removed.

Shown without plunger 110 mounted within it (FIGS. 13-15), split tubular member 122 includes a pair of elongated slots 124 spaced about 40-50 degrees away from each other around the circumference of tubular member 122 (FIG. 13). Slots 124 extend virtually the entire length of tubular member 122 forming a flexible tab 126 between them. Tab 126 includes a threaded portion 128 which engages threaded portion 116 of knob 118 such that plunger 110 can be threaded inwardly and outwardly of bore 120.

Figure 15:
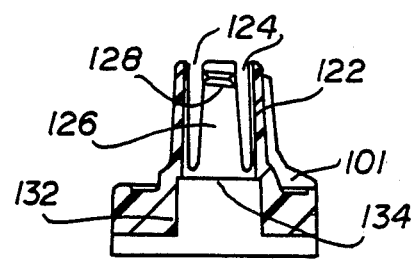
FIG. 15 is a section taken along the plane of line 15—15 of FIG. 13.
Figure 14:
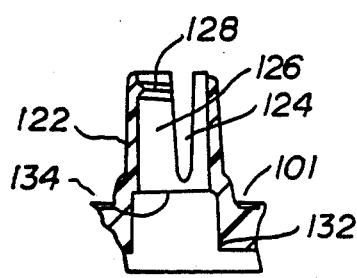
FIG. 14 is a section taken along the plane of line 14—14 of FIG. 13.

However, plunger 110 can be quickly shifted inwardly and outwardly of bore 120 without having to thread plunger 110. This can be accomplished simply by pushing plunger 110 inwardly or pulling it outwardly of bore 120. When pushed inwardly from the open position shown in FIG. 12, threaded portion 128 will slide over threaded portion 116 because tab 126 is flexible since upper housing portion 101 is made from a plastic material. As can be seen, flexible tab 126 will flex outwardly under axial upward or downward force applied to plunger 110, thereby permitting threads 116 to slide over thread 128 on tubular number 122. As shown in FIGS. 13-15, tab 126 is the only part of tubular member 122 which is threaded, allowing threads 116 to slide over thread 128 due to the flexiblility of tab 126.

To prevent plunger 118 from being pulled from completely out of bore 120, stem 114 includes plurality of upwardly oriented barbs 130. In addition, bore 120 is provided with an expanded diameter portion 132 which forms an annular shoulder 134 within bore 120. Barbs 130 are positioned to be received within expanded diameter portion 132, and engage shoulder 134 when plunger 110 is in the fully opened position illustrated in the FIG. 12. Barbs 130 are oriented, however, so as to allow stem 114 to be inserted through the upper narrow diameter end of bore 120. When stem 114 is so inserted, barbs 130 will resiliently deflect inwardly of stem 114 as they pass through the narrow diameter portion of bore 120 until barbs 130 pass shoulder 134. When they pass shoulder 134, barbs 130 they expand outwardly and prevent plunger 110 from being pulled completely out of bore 120.

To allow head 120 to be pushed downwardly into sock 109 without compressing air in the bottom of the sock, head 112 is provided with a groove 136 which allows air to pass around head 112 as head 112 is pushed inwardly of or urged outwardly from sock 109.

Although the best mode contemplated for carrying out the present invention has been herein shown and described, it will be apparent that modification and variation can be made without departing from what is regarded to be the subject matter of the invention.

What is claimed is:

1. A liquid flow regulator, comprising:
a housing having an axial bore, an inlet adjacent one end of the bore, an outlet at the opposite end of the bore, and at least one axial groove opening endwise into the inlet and laterally of the bore into the bore, said groove having at least one dimension that tapers from the inlet to the bore so that the groove cross-sectional area gradually decreases to nothing where the groove merges into the bore;
an elastomeric member fitted within the bore;
a plunger movable axially of the bore, the lower end of the plunger being positioned within the elastomeric member for expanding the elastomeric member radially outward into sealing engagement with the housing adjacent the bore, whereby flow through the groove and the bore is regulated by the axial position of the plunger and the minimum cross-sectional area of the tapered, axial groove at the axial location where the elastomeric member seals the bore; and
means forming a threaded passageway above the bore for receiving the upper end of the plunger, and thread means being provided on the upper end of the plunger for engagement with the threads in said passageway for controlling the axial movement of the plunger during rotation thereof, the connection between said thread means and the passageway being laterally flexible so that the plunger can be directly moved axially without rotation thereof to quickly move the regulator from a fully open condition to a fully closed condition or vice versa.

2. The liquid flow regulator of claim 1 having a plurality of axial grooves opening endwise into the inlet and laterally of the housing into the bore, said grooves being tapered from the inlet end to the bore so that the cross-sectional area of each groove gradually decreases to nothing where the groove merges into the bore, said grooves having different axial lengths, whereby axial adjustment of the plunger sequentially opens and closes flow passage from the grooves through the bore to the bore outlet.

3. The liquid flow regulator of claim 1 wherein said plunger has an enlarged head at its lower end for compressive engagement with said elastomeric member within the bore.

4. The liquid flow regulator of claim 1 wherein the upper end of the plunger is split so that said thread means can be flexed inwardly out of engagement with the threads in said passageway when the plunger is non-rotatively moved to place the regulator in a fully open or fully closed position.

5. The liquid flow regulator of claim 3 wherein the upper end of the plunger is longitudinally split into two stem portions, said thread means comprising at least one tooth provided on one of said stem portions, said one stem portion being adapted to flex inwardly under the impetus of an axial force on the plunger to disengage the tooth from the threads in said passageway.

6. The liquid flow regulator of claim 5 wherein the other of said stem portions is provided with an enlarged head for gripping engagement by an external actuator member.

7. The liquid flow regulator of claim 1 wherein said connection between said thread means and said passageway includes a tubular member forming said passageway, said tubular member having a flexible tab.

8. The liquid flow regulator of claim 7 wherein said plunger includes a threaded portion, and said flexible tab includes a threaded portion, whereby said plunger can be axially moved without rotation thereof to move the regulator quickly from a fully open condition to a fully closed condition or vice versa.

9. The liquid flow regulator of claim 1 wherein said passageway includes an enlarged diameter portion forming a shoulder therein, and said plunger includes means for engaging said shoulder to prevent said plunger from being moved completely out of said passageway.

10. The liquid flow regulator of claim 9 wherein said engagement means includes a barb.

11. The liquid flow regulator of claim 7 wherein said passageway includes an enlarged diameter portion forming a shoulder therein, and said plunger includes means for engaging said shoulder to prevent said plunger from being moved completely out of said passageway.

12. The liquid flow regulator of claim 11 wherein said engagement means includes a barb.

13. A liquid flow regulator, comprising:

a housing having an axial bore said housing having an inlet and an outlet;

plunger means positioned and moveable within said bore, said plunger means having valve means associated therewith to open or close said outlet upon movement of said plunger means; and threaded connection means between said plunger means and said housing so that said plunger can be threadably positioned at selected positions within said bore to regulate flow through said outlet, said threaded connection means having a flexible element which disengages said threaded connection means upon application of axial force to said plunger means so that said plunger can be directly moved without rotation thereof from a fully open to a fully closed position or vice versa.

14. The liquid flow regulator of claim 13 wherein said valve means includes an elastomeric sock fitted in said bore and an enlarged head positioned on said plunger.

15. The liquid flow regulator of claim 13 wherein flexible threaded connection means includes a flexible tab on one of said plunger and said housing, said tab including a threaded portion.

16. The liquid flow regulator of claim 15 wherein said flexible tab is on said plunger, said tab being laterally flexible so that said plunger can be axially moved to fully open or close said regulator.

17. The liquid flow regulator of claim 15 wherein said flexible tab is on said housing.

18. The liquid flow regulator of claim 17 further including means for forming a passageway above said bore for receiving one end of said plunger, said flexible tab being formed by a pair of spaced slots extending longitudinally of said passageway forming means.

* * * * *